United States Patent [19]
Younker

[11] Patent Number: 5,643,283
[45] Date of Patent: Jul. 1, 1997

[54] SURGICAL POUCH

[76] Inventor: Marlin E. Younker, 9905 Hobart Rd., Waite Hill, Ohio 44094

[21] Appl. No.: 357,368

[22] Filed: Dec. 15, 1994

Related U.S. Application Data

[63] Continuation of Ser. No. 215,009, Mar. 21, 1994, abandoned, which is a continuation of Ser. No. 966,902, Oct. 26, 1992, abandoned, which is a continuation of Ser. No. 816,900, Jan. 3, 1992, abandoned.

[51] Int. Cl.⁶ ..................................................... A61B 17/24
[52] U.S. Cl. ........................ 606/114; 606/127; 600/37
[58] Field of Search .......................... 606/1, 37–50, 606/106–114, 127, 128, 151, 213; 604/27

[56] References Cited

U.S. PATENT DOCUMENTS

| | | | |
|---|---|---|---|
| 30,471 | 10/1860 | Dudley | 606/127 |
| 974,879 | 9/1910 | Gwinn . | |
| 1,609,014 | 11/1926 | Dowd . | |
| 1,615,494 | 1/1927 | Waring . | |
| 1,931,740 | 10/1933 | Ryan . | |
| 2,043,782 | 6/1936 | Sprosty . | |
| 2,115,298 | 4/1938 | Brown . | |
| 3,244,169 | 4/1966 | Baxter . | |
| 3,472,230 | 10/1969 | Fogarty . | |
| 3,834,392 | 9/1974 | Lampman et al. . | |
| 3,908,661 | 9/1975 | Kramer . | |
| 3,920,179 | 11/1975 | Hall . | |
| 4,112,932 | 9/1978 | Chiulli . | |
| 4,217,890 | 8/1980 | Owens . | |
| 4,295,464 | 10/1981 | Shihata . | |
| 4,428,375 | 1/1984 | Ellman . | |
| 4,447,227 | 5/1984 | Kotsanis . | |
| 4,557,255 | 12/1985 | Goodman | 606/127 |
| 4,619,260 | 10/1986 | Magill et al. . | |
| 4,638,802 | 1/1987 | Okada | 606/47 |
| 4,785,826 | 11/1988 | Ward . | |
| 4,790,812 | 12/1988 | Hawkins, Jr. et al. . | |
| 4,798,213 | 1/1989 | Doppelt . | |
| 4,865,017 | 9/1989 | Shinozuka . | |
| 4,905,691 | 3/1990 | Rydell . | |
| 4,927,426 | 5/1990 | Dretler . | |
| 4,991,593 | 2/1991 | LeVahn . | |
| 4,997,435 | 3/1991 | Demeter . | |
| 5,018,877 | 5/1991 | Kantz . | |
| 5,026,371 | 6/1991 | Rydell et al. | 606/47 |
| 5,037,379 | 8/1991 | Clayman et al. | 604/27 |
| 5,074,867 | 12/1991 | Wilk . | |
| 5,084,054 | 1/1992 | Bencini et al. | 606/113 |
| 5,147,371 | 9/1992 | Washington et al. . | |
| 5,163,942 | 11/1992 | Rydell | 606/1 |
| 5,190,542 | 3/1993 | Nakao et al. . | |
| 5,190,555 | 3/1993 | Wetter et al. | 606/114 |
| 5,201,740 | 4/1993 | Nakao et al. | 606/114 |

FOREIGN PATENT DOCUMENTS

| | | | |
|---|---|---|---|
| 0025796 | 1/1884 | Brazil | 606/127 |
| 3522649 | 1/1986 | Germany | 606/127 |
| 3913935 | 10/1990 | Germany | 606/127 |

OTHER PUBLICATIONS

Atlas of Endo Cholecystectomy, by Zucker and Bailey, 1990, pp. 1–14.

*Primary Examiner*—Glenn Dawson

[57] ABSTRACT

A surgical device for retrieving an object from inside a body. The device includes a shaft, a compressible pouch for receiving the object positioned adjacent the first end of the shaft. The pouch includes a mouth which may be opened and closed. An introducer sleeve is slidably positioned along the shaft for enclosing the pouch. A slotted support member having a first end affixed to the second end of the shaft, is also provided. Further, a slidable handle member is slidably positioned along the slotted support member, and an interconnecting member extends through the shaft and is interconnected with the handle, pouch and the slotted member for closing and opening the pouch, such that sliding the handle along the slotted member operates to open and close the pouch of the device.

21 Claims, 6 Drawing Sheets

SURGICAL POUCH

This is a continuation of application Ser. No. 08/215,009 filed Mar. 21, 1994, abandoned, which is a continuation of Ser. No. 07/966,902 filed Oct. 26, 1992, abandoned which is a continuation of Ser. No. 07/816,900 filed Jan. 3, 1992, now abandoned.

BACKGROUND OF THE INVENTION

Historically, surgical removal of internal organs such as a gallbladder, required a wide incision through the abdominal tissue. The length of the incision contributed to long recovery periods and more scar tissue. Recent surgical techniques have progressed to the use of a number of smaller percutaneous puncture sites, typically four to five. The surgery is accomplished by the introduction of a camera attached to a rigid fiber optic telescope through one of the sites. The camera permits the surgeon and the entire operating room group to view the surgery. Other incisions are made to accommodate surgical instruments such as grasping forceps, and electro-surgical devices or laser devices.

Once an organ or other tissue has been detached, it must be removed from the body via one of the sites. Simply removing the tissue by grasping with forceps presents several problems. First, the tissue may be difficult to grasp and hold during removal. Additionally, the tissue may be difficult to remove through the site, particularly if the tissue is larger than the hole. In the case of gallbladder removal, for example, there is the further problem of organ contents spilling out into the body cavity. When an organ, particularly a gallbladder is removed through the site, the contents of the gallbladder, that is the gallstones, tend to spill out into the body cavity. The gallstones must then be retrieved by the surgeon. This retrieval is a laborious and time consuming process often requiring additional surgical time.

As set forth in U.S. Pat. No. 5,037,379, attempts have been made to solve these problems by introducing a surgical bag to capture the organ or tissue, and thereby facilitate its removal. Unfortunately, such attempts have not included one handed operation, nor a form that provides for easy insertion and removal of the device into and out of the body.

SUMMARY OF THE INVENTION

Prior art retrieval devices employing bags or pouches which could be closed to retain objects deposited in them were sometimes difficult to deploy because the pouch or bag failed to open properly. Furthermore, bags or pouches often had to be reinserted and redeployed to remove all objects from the patient's body. In such cases, the retrieval bags or pouches frequently failed to open fully when redeployed.

The present invention provides a new and improved surgical device for retrieving an object such as internal organs, tissues or foreign objects from inside the body. The surgical device is capable of easy introduction into the body, one handed operation, and which may be closed to prevent the retrieved object and its contents, from escaping. The device may be inexpensively produced so as to render the device disposable. The device comprises an operating assembly including a shaft portion interconnected with a closure portion, and an interconnecting member. The closure portion includes a support member and a slidable member mounted on the support member. In the preferred embodiment of the present invention, the support member is a slotted member affixed to the shaft. The shaft and slotted support member each include a longitudinal bore extending therethrough. A compressible pouch for receiving the object is also provided positioned adjacent the shaft, and has a mouth which may be opened and closed. Additionally, an introducer sleeve is provided slidably positioned along the shaft for enclosing the pouch. A handle is preferably provided as a part of the slidable member, which is slidably supported along the support member.

The interconnecting member preferably comprises a flexible member having a bend at a substantially central portion of the member, and which is attached on one end to the slidable member and on a second end to the support member. The interconnecting member extends through the shaft, and surrounds the mouth of the pouch enclosed within a pocket thereof. By sliding the handle along the slotted member in one direction or the other, which may be done with one hand, the interconnecting member operates to close or open the mouth of the pouch. Also, the device may be inserted into the body using one hand.

The invention also relates to a method for retrieving internal organs, tissues, stones and debris.

DETAILED DESCRIPTION OF THE INVENTION

The present invention, is a surgical device that may be used to retrieve objects, primarily tissues, polyps, internal organs such as a gallbladder, appendix, resected colon, ovaries and even foreign objects. The device is particularly useful in removing gallbladders or infected organs because the device can be closed to prevent the contents of the gallbladder, such as gallstones, from escaping into the body cavity. The device may be operated by the surgeon using one hand, leaving the other hand free to perform other functions, which is a substantial benefit during surgery.

The device, indicated generally at reference numeral 10, constructed in accordance with the present invention, is schematically illustrated in FIG. 1–5 of the Drawings. The device 10 comprises an operating assembly 11, which preferably includes a shaft portion 12 and a closure portion 13 having a support member 18 engaged with the shaft portion, a slidable member 19 supported along the support member, and an interconnecting member 22. A compressible pouch 14 for capturing the objects to be removed, an introducer sleeve 16 for enclosing the pouch during insertion of the device, and a handle 20 for operating the device, are also provided.

Figure 4:
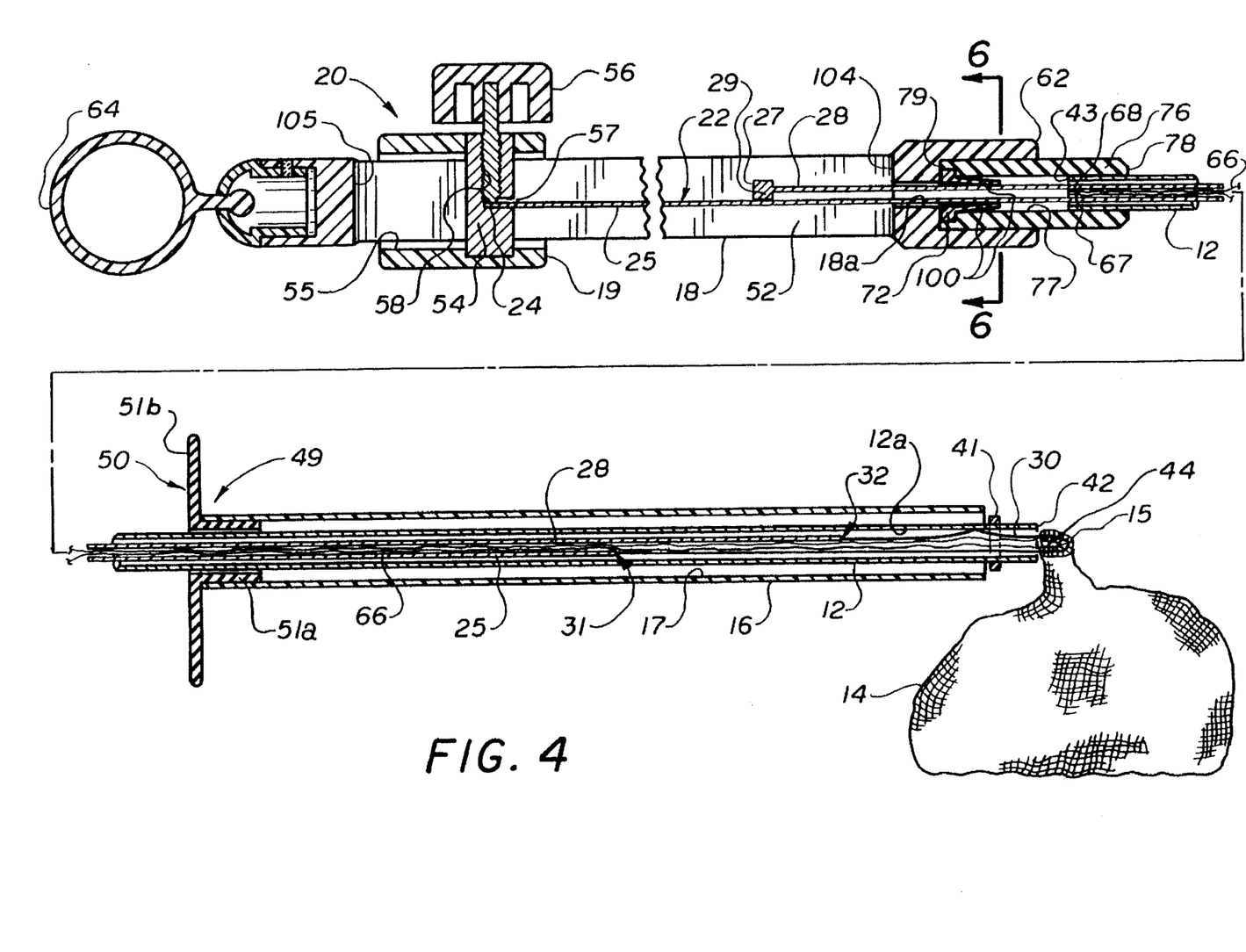
FIG. 4 is a cross-sectional view of the invention with the pouch deployed in the mouth closed position.
Figure 5:
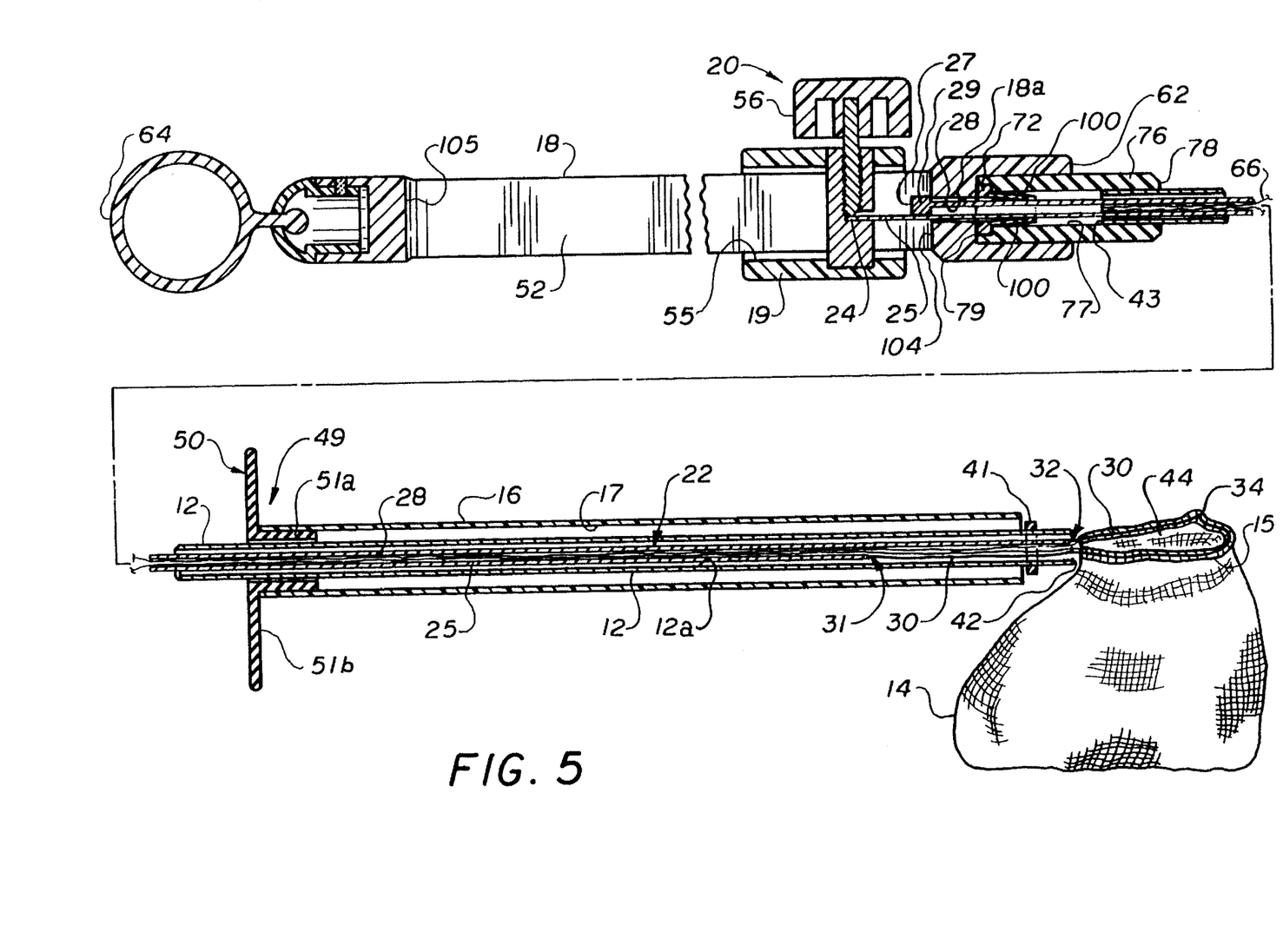
FIG. 5 is a cross-sectional view of the invention with the pouch deployed and in the mouth open position.
Figure 6:
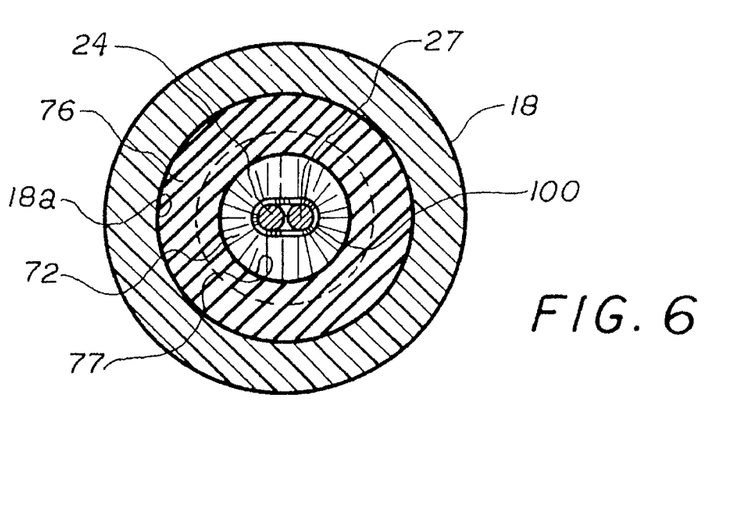
FIG. 6 is a cross-sectional view of the invention, taken along line 6—6 of FIG. 4.

As best illustrated in FIGS. 4–5, the shaft portion 12 of the operating assembly 11 has two ends and a longitudinal bore 12a. The shaft 12 may be made of a rigid material, such as metal or plastic. As illustrated herein, the shaft 12 is stainless steel. The first end 42 of the shaft is positioned adjacent the pouch 14 and the second end 43 of the shaft portion 12 is affixed to the support member 18.

The closure portion 13 of the operating assembly 11 includes the slidable member 19 supported on the support member 18, and the interconnecting member 22 engaged therebetween. In the illustrated embodiment of the present invention, the support member 18 is illustrated as a slotted member. However, an unslotted cylindrical member could also be used. The second end 43 of the shaft 12 is engaged within a first end 62 of the slotted member or slotted support member 18 is affixed to T. The slotted member 18 includes a slot 52, having a first and second ends 105. The slot 52 forms an opening through the member, and includes a bore 18a extending from the first end 62 to the first end 104 of the slot. As illustrated, the shaft portion 12 and closure portion 13 of the operating assembly 11 are interconnected such that the bore 18a of the slotted member 18 is aligned with the bore 12a of the shaft portion 12. As further illustrated, the shaft portion 12 is connected to the slotted support member 18 by a connecting sleeve 76.

The connecting sleeve 76 which interconnects the shaft portion 12 and closure portion 13 has a longitudinal bore 77, and first and second ends 78, 79. The end 43 of shaft 12 is press-fit into engagement with the first end 78 of the connecting sleeve 76. Likewise, the second end 79 of the connecting sleeve 76 is press-fit into engagement with the first end 62 of slotted member 18, to join the shaft and closure portions of the operating assembly.

Figure 7:
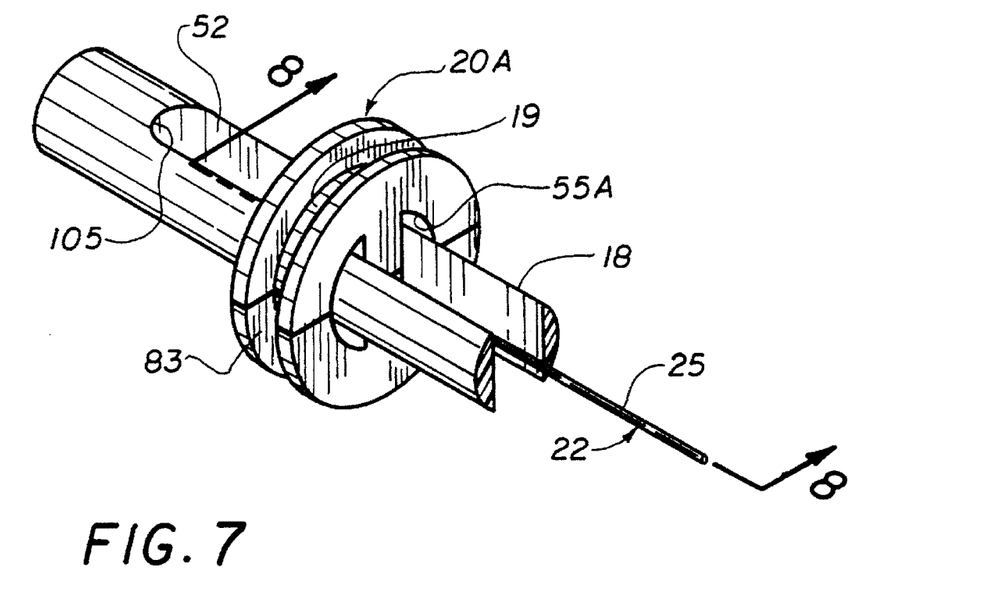
FIG. 7 is a perspective view of an alternative embodiment of the handle of the invention.
Figure 8:
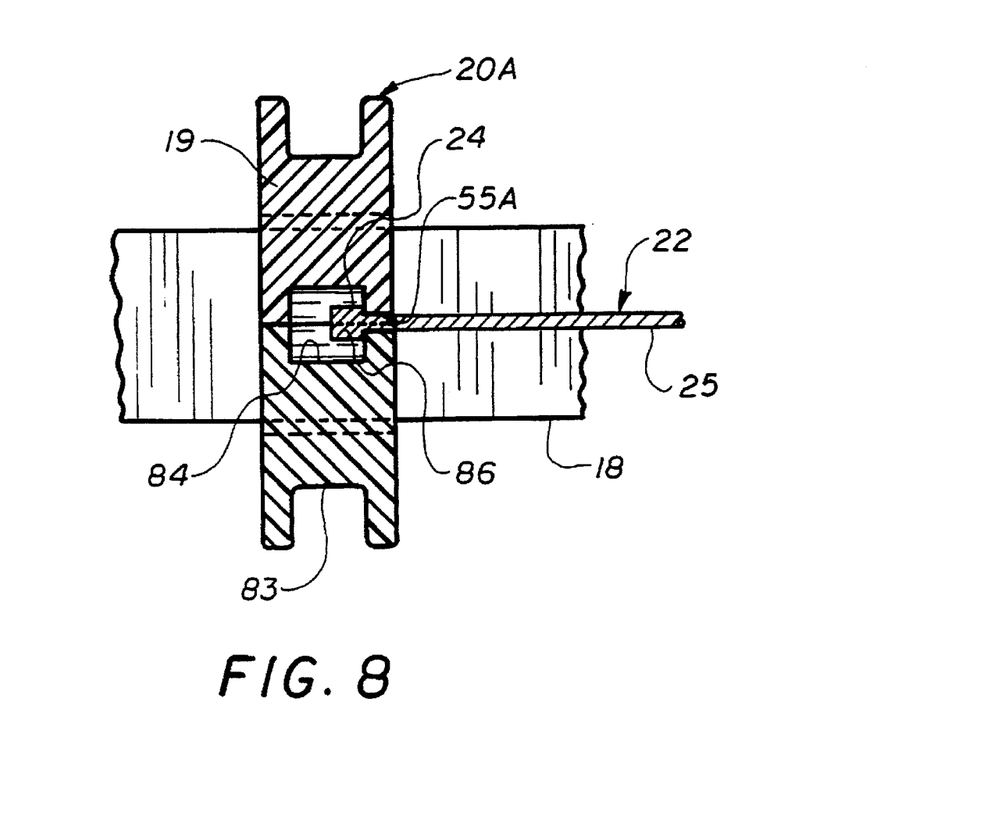
FIG. 8 is a cross-sectional view of the invention taken along line 8—8 of FIG. 7.

The slidable member 19 of the preferred and illustrated embodiment includes a handle 20, 20A for slidably moving the slidable member along the support member 18 to open and close the pouch 14. The slidable member 19 has a longitudinal bore 55, 55A, and may be made of any rigid material, such as metal or plastic. The slidable member is slidably supported along the slotted support member 18. In the illustrated embodiment of FIGS. 1, 3, 4 and 5, the slidable member 19 is adapted for grasping as a handle 20, and includes two finger gripping holes 21a and 21b to accommodate the operator's fingers. In another embodiment shown in FIGS. 7 and 8, the slidable member 19 is provided with a handle 20A comprising a spool having an annular groove 83 to accommodate the operator's fingers.

As illustrated in FIGS. 4 and 5, the slidable member 19 includes a central shaft 54 which extends through a longitudinal bore 55, and through the slot 52 of the slotted support member 18. Although the interconnecting member 22 may be secured with the slidable member 19 by any conventional method, in the illustrated device, the shaft 54 includes a hole 57 to receive an end of the interconnecting member 22. Further, the shaft 54 has a set screw 56 engaged within a threaded bore 58 for holding the interconnecting member within the slidable member 19. In another embodiment, shown in FIGS. 7 and 8, the longitudinal bore 55A, of the slidable member 19 has a chamber 84 for receiving the interconnecting member 22, which has a stop 86 on the end 24 thereof to resist removal from the chamber 84 via the bore 55A.

The interconnecting member 22 of the operating assembly 11 is a continuous elongate member having a first end 24 engaged with the slidable member 19 having the handle 20, 20A and a second end 27 engagable with the slotted support member 18. In the preferred embodiment illustrated in FIGS. 4 and 5, the interconnecting member includes a bend 34 intermediate the first and second ends 24, 27. A first arm 25 is defined between the first end 24 and bend 34, and a second arm 28 is defined between the bend and second end 27. The arms 25, 28 are generally parallel. The end 24 of arm 25 is connected to the handle 20, 20A. Thus, arm 25 extends from the handle 20, 20A through the slot 52 of the slotted member 18, the bore 18a of the slotted member 18, and the bore 12a of the shaft portion 12, such that the bend 34 extends from the first end 42 of the shaft portion.

From the bend 34, the second arm 28 extends back into the shaft bore 12a, slotted member bore 18a and slot 52 adjacent the first arm 25, and the second end 27 is engaged through the bore 18a and includes a stop 29 to resist removal of the end 27 from the slotted member 18. The arms 24, 27 must be of a sufficiently rigid material to maintain their structure during operation of the device. In the illustrated embodiment herein, the arms 24 and 27 are 19 gauge, 302 stainless steel hypodermic tubing. Additionally, the diameter of the bore 12a must be sufficient to accommodate movement of the arms 24, 27 of the interconnecting member, while the outside diameter of the shaft portion 12 must be sufficient to be engaged within a bore 17 of the introducer sleeve 16. Preferably, the end 42 of shaft 12 is adapted, for example, with a flange, flair or ring 41, to engage end 49 of introducer sleeve 16, so as to prevent the end 42 of shaft 12 from sliding out of end 49 of introducer sleeve 16. The end 42 of shaft 12 may alternatively be compressed or crimped to provide the end 42 with an elliptical cross-sectional configuration to prevent the shaft 12 from sliding off the introducer sleeve 16.

In the preferred and illustrated embodiment, the portions of the interconnecting member 22 surrounding the bend 34 are of a different but continuous material comprising a flexible member 30. As shown in FIG. 4, the flexible member 30 is located within the arm 25 of interconnecting member 22 beginning at an end 31, and ends within the arm 28 at an end 32. The bend 34 is formed within the flexible member 30 and is located along the interconnecting member at a location such that movement of the slidable member 18 to the position shown in FIG. 5 adjacent the end 62 of the slotted member, forms the mouth 44 of the pouch to a D-shaped configuration, as further discussed below. The member 30 is preferably made of a flexible material such as a flexible braided wire. As illustrated, the flexible member 30 is 0.024, 1×7 braided stainless steel cable, available from National Standard Company. The flexible member 30 is enclosed by and extends through a pocket 15 of pouch 14.

Alternatively, the entire interconnecting member 22 or the flexible member 30 may be of any suitable material, such as a flat wire spring having a sharp bend, a round monofilament wire, a multistrand polymer, or any combination thereof.

The pouch 14 may be made of any compressible material. The pouch may be of a permeable material having a pore size to permit fluids, such as blood and bile, to pass through the pouch 14. For example, the pouch 14 may be of Dacron™ polyester. Alternatively, the pouch 14 may be of a nonpermeable material, such as polyurethane, silicone, or polyvinyl chloride, which will not permit any of the bag contents from escaping. The pouch 14 must be sufficiently sized and compressible so as to permit the pouch 14 to be enclosed within the introducer sleeve 16.

The pouch 14 includes the opening or mouth 44, which is surrounded by the pocket 15. A portion of the operating assembly interconnecting member 22, including the bend 34, is enclosed within the pocket 15. The mouth 44 of the pouch 14 may be moved by the interconnecting member between an open position in FIG. 5 and a closed position in FIG. 4. In addition, the flexible interconnecting member 30 is sufficiently rigid to support the pouch 14 when it is suspended within the body cavity. The pouch 14 is retained in proximity to the end 42 of the shaft portion 12 by a tether 66. Tether 66 is a loop of flexible material having two ends 67 and 68. In the illustrated embodiment, the tether 66 is made of 0.010 mil 304 stainless steel wire. The tether 66 secures the pouch in position with respect to the shaft by engaging a corner of the pouch 14 intermediate the tether ends 67, 68. The ends are then secured in engagement intermediate the end 43 of the shaft portion 12 and the sleeve 76. By securing the pouch using the tether 66, the location of the pouch mouth is always immediately adjacent the end 42 of the shaft portion 12.

The introducer sleeve 16 has a longitudinal bore 17, and is slidably positioned along the shaft portion 12 of the operating assembly 11. The sleeve 16 is preferably made of a rigid material such as a metal or plastic, for example, 0.01 mil Teflon™ tubing. The introducer sleeve 16 must be of a sufficient internal diameter and length to enclose the compressed pouch 14 and portions of the interconnecting member 22. The external diameter of the introducer sleeve 16 must also be sufficient to permit the introducer sleeve 16 to pass through the bore of a trocar T during use of the device 10. A trocar T is a surgical device having a central bore, which is inserted through the body B wall to provide and maintain an opening or site between the exterior and the interior of the body. The use and design of the trocar are well known to those of ordinary skill in the art.

The introducer sleeve 16 is adapted at one end so as to engage the opening of the trocar T. Additionally, the first end 42 of the shaft portion 12 is adapted, as previously discussed, to prevent the sleeve from being removed from engagement on the shaft. Another adaptation to prevent removal of the sleeve from the shaft portion, and further entry of the introducer sleeve 16 into the bore of the trocar T, is a stopper 50. As illustrated herein, the stopper 50 has one end 51a modified in the form of a disk. The other end 51a of stopper 50 is press-fit into engagement with the end 49 of the introducer sleeve 16.

Typically, surgical procedures include introducing carbon dioxide gas through an insulflator device to inflate the abdominal cavity. In the preferred embodiment, a conventional valve 72 is provided in the operating assembly located at end 79 of connecting sleeve 76, as shown in FIG. 5. The valve 72 includes flaps 100 which are engaged to provide a seal between the shaft portion 12 and the closure portion 13 which prevents gas in the body cavity from escaping through the shaft portion. The valve may be made of buna, vitian or silicone, and must be constructed so as not to interfere with movement of the interconnecting member 22 which passes through the valve 72 and flaps 100.

USE OF THE INVENTION

Figure 1:
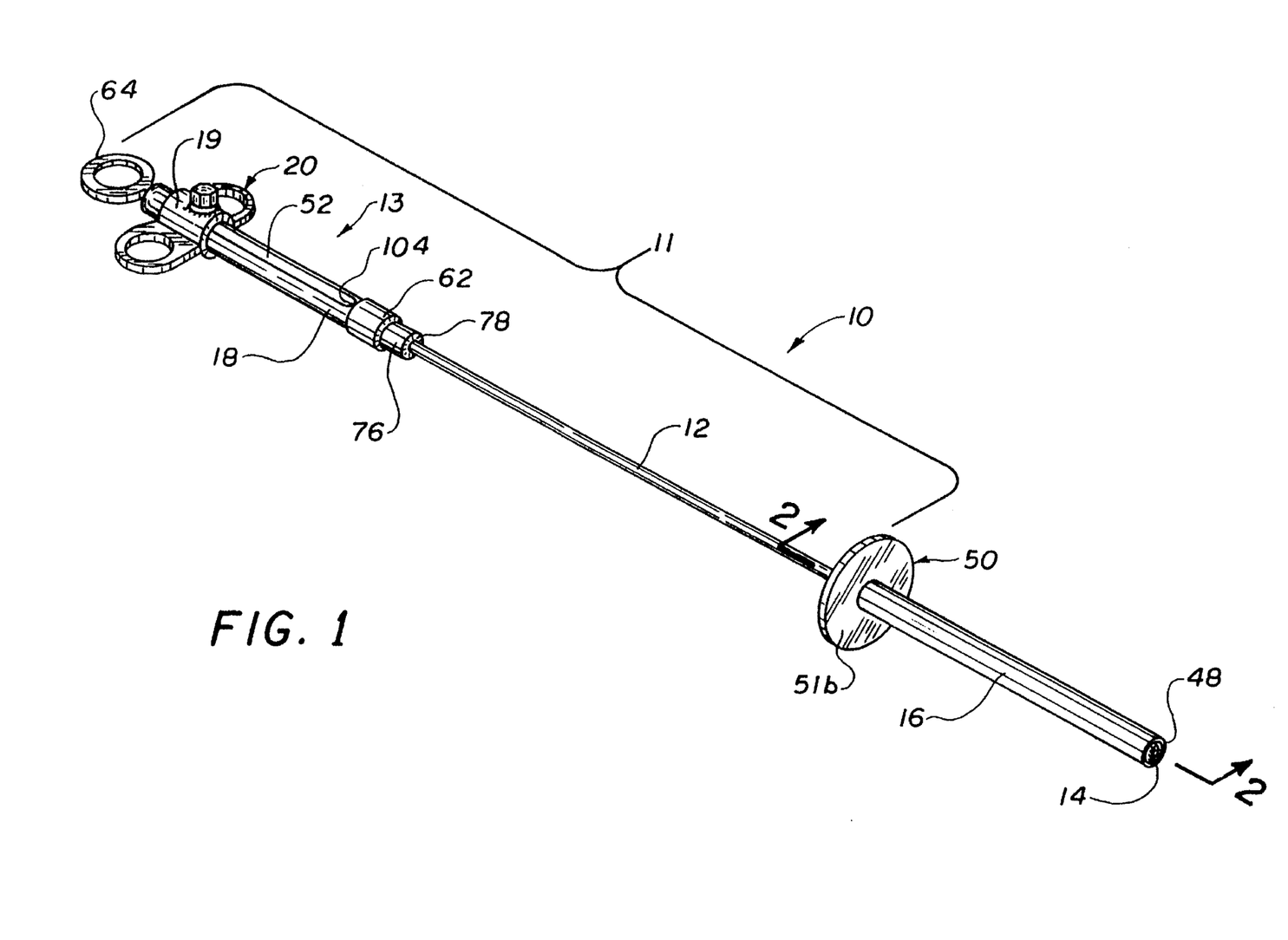
FIG. 1 is a schematic perspective view of the invention, prepared for insertion into the body cavity.
Figure 2:
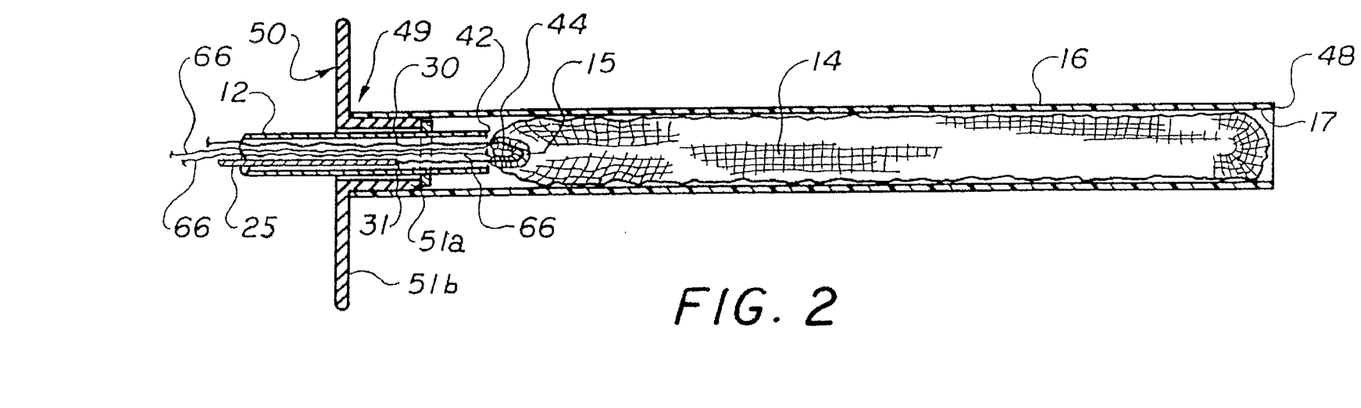
FIG. 2 is a cross-sectional view of the invention, taken along the line 2—2 of FIG. 1.
Figure 3:
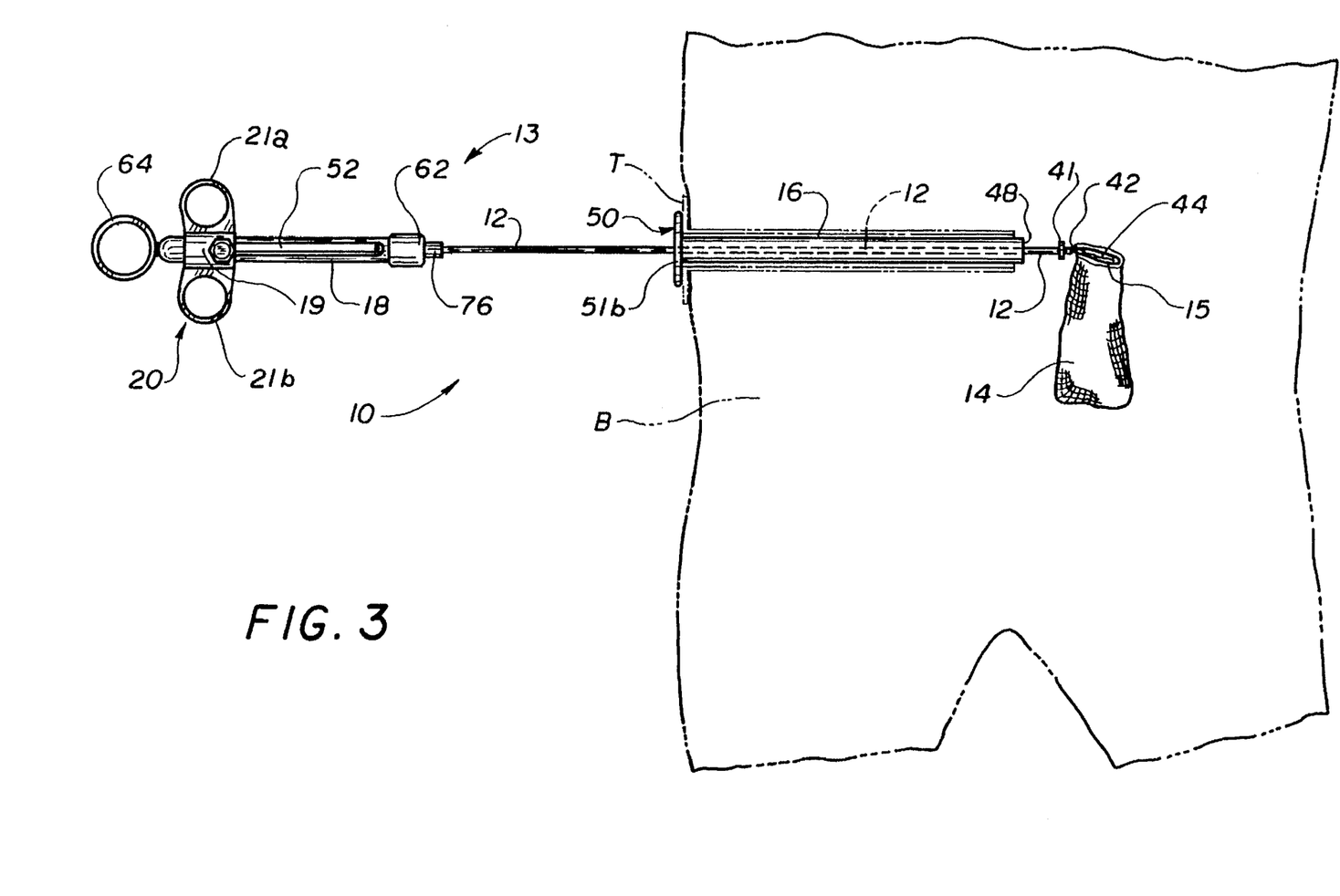
FIG. 3 is a side view of the invention shown inserted into the environment of a body cavity shown in phantom and with the pouch deployed and in the mouth open position.

Before inserting the device 10 into the body, the device 10 must be prepared for insertion. The handle 20, 20A is drawn back, away from the pouch 14 so that the pouch mouth 44 is closed, and pocket 15 is tightly gathered along a portion of the flexible member 30 adjacent the end of the shaft portion. As illustrated in FIG. 2, the introducer sleeve 16 is then slidably engaged over the pouch 14 to enclose the pouch. The invention 10 is, preferably, initially inserted into the body B as illustrated in FIG. 3, via a trocar T. It may also be possible to insert the invention directly into a site in the body wall.

The present invention may be inserted into the body cavity B by pushing the device 10 into the bore L of trocar T. As the invention is pushed into bore L of the trocar T, the disk 50 of the introducer sleeve 16 is eventually engaged by the trocar T. This engagement prevents the introducer sleeve 16 from entering the bore L of the trocar any further. However, continued pushing of the device 10 into the body causes the pouch 14 and the shaft 12 to slide through the introducer sleeve 16, beyond an end 48 of the introducer sleeve 16. As a result, the pouch 14 is no longer enclosed by the introducer sleeve 16, and hangs freely within the body cavity as in FIG. 3. A portion of the end 42 of the shaft 12 also typically projects into the body cavity; however, this depends on the depth the device 10 has been inserted into the trocar.

The pouch mouth 44 is opened by manually sliding the slidable member 19 using the handle 20, 20A along the slotted member 18 towards the body B. The movement of the slidable member 19 towards the body using the handle 20, 20A pushes the first end 24 of arm 25 toward the body, within the slot 52, valve 72, bore 18a of the slotted member 18, and the bore 12a of the shaft portion 12. When the stop 29 forming the end 27 of the arm 28 abuts the slotted member bore 18a, the length of the arms 25, 28 extending from the shaft is equally spaced from the end 42 of the shaft to the bend 34.

Further movement extends the portion of the first arm 24 extending from the shaft 12, which at this location is the flexible member 30, to a length greater than that portion of the fixed arm 28 extending from the shaft, and into the pocket 15 surrounding the pouch mouth 44. The extending arm 25 of the flexible member 30 springs open, such that the extension of the first arm 24 into the pocket 15 forms a loop which expands the mouth 44 to open the pouch 14.

In the open position, the length of the extended first arm 24 extending from the shaft is greater, relative to the bend 34, than the length of the second or fixed arm 28 extending beyond the end 42 of the shaft. When the slidable member is positioned adjacent the first end 104 of the slot 52, the mouth 44 is fully opened. This is illustrated in FIG. 5.

The surgeon may then place the tissue into the pouch 14. One can envision many alternate ways of accomplishing the surgery. The pouch 14 may be opened first then the tissue is cut, or the tissue may be cut then the pouch 14 is opened.

Once the object to be retrieved is placed in the pouch 14, the mouth 44 is then closed by sliding the handle 20 along slotted member 18, away from the body, that is, toward end 64 of slotted member 18 engaged with the second end 105 of the slot 52. This movement causes the flexible member 30 to be pulled back through the bore 13 of the shaft 12. As a result, the extended arm 24 is first drawn back into the shaft portion 12, until the portion of the arms 24, 27 extending from the shaft are equal with respect to the bend 34. Both arms are then further retracted into the shaft bore 18a, thereby closing the pouch mouth 44. Thus, the contents of the pouch 14, such as gallstones, are prevented from escaping. This is illustrated in FIG. 4.

The device 10 is removed by pulling the device away from the body. Two alternate methods for removing the device are envisioned. In the preferred method, the device 10 and the trocar T are entirely withdrawn from the body B by pulling away from the body until the mouth 44 of the pouch 14 is removed from the body B via the site. The mouth 44 is then opened and the contents are removed by suction or morcelated. This method may be used where the contents of the pouch 14 are of sufficient size so as to prevent the pouch 14 from being drawn back into the bore 17 introducer sleeve 16. This method may also be used where the pouch 14 is made of nonpermeable material. A nonpermeable pouch does not permit fluids within the pouch 14 to be squeezed out as the operator attempted to draw the pouch 14 back into the introducer sleeve 16, and thus may prevent removal of the pouch via the introducer sleeve and trocar.

A second method may be used where the object to be removed from the body is smaller than the diameter of the introducer sleeve 16. In this method the trocar is not removed from the body with the device. Instead, as the device 10 is pulled away from the body, the pouch 14 is pulled back into the bore 17 of introducer sleeve 16. The pouch 14 and its contents are compressed as they are pulled into the introducer sleeve 16, causing the liquid contents to be squeezed out of the pouch 14. As the operator continues to pull the invention 10 away from the body, the pouch 14 is pulled through the introducer sleeve 16, which is then removed from the trocar T.

Although the use of this invention has been described in assisting surgical procedures, the device may also be used to retrieve objects in other situations. While a preferred embodiment of the invention has been disclosed in detail, along with certain alternative constructions and arrangements, the present invention is not to be considered limited to the precise constructions disclosed herein. Various adaptations, modifications and uses of the invention may occur to those skilled in the art to which the invention relates, and the invention is to cover all such adaptations, modifications and uses falling within the spirit and scope of the following claims.

What I claim is:

1. A surgical device for retrieving an object from a body, comprising, an operating assembly including a shaft portion having a longitudinal bore extending between first and second ends, a closure portion having a support member engaged with said second end of said shaft portion, a slidable member slidably mounted on said support member for operation of said assembly, and a flexible elongate interconnecting member secured at a first end with said slidable member and engagable with said support member at a second end, a compressible pouch for receiving the object, having a mouth portion secured adjacent said shaft portion first end, and which is movable between an open position and a closed position upon operation of said slidable member, said pouch comprising a pocket surrounding said mouth portion, an introducer sleeve slidably mounted on said shaft portion, and having a longitudinal bore for housing said pouch, and said interconnecting member disposed within said shaft portion and said pouch pocket such that manual movement of said slidable member with respect to said support member moves said pouch mouth portion between open and closed positions, said interconnecting member having a bend intermediate its first and second ends to form a first arm between said first end of said interconnecting member and said bend, and a second arm between said bend and said second end, of said interconnecting member, said first and second arms engaged within said shaft portion bore and said bend and portions of said first and second arms engaged within said pouch pocket, said interconnecting member second end comprising a stop for engaging said support member to permit limited movement of said second end with respect to said support member.

2. The surgical device of claim 1, wherein said operating assembly includes a seal device valve for engagement with said interconnecting member for limiting gas passage from said shaft portion to said closure portion during use of the surgical device.

3. The surgical device of claim 1, wherein said mouth portion of said pouch has a substantially D-shaped configuration when in the open position.

4. A surgical device for retrieving an object from a body, comprising:

a. a shaft having a longitudinal bore therethrough;

b. a compressible object receiving pouch having a mouth which may be opened and closed;

c. a closure for closing and opening said pouch comprising, a support member attached to said shaft, a slidable member slidably attached to the support member, and an interconnecting member interconnected with said slidable member;

said interconnecting member comprising a flexible elongate member extending through said shaft and engaged with said pouch surrounding said mouth, and having first and second ends and a bend intermediate said ends, said first end engagable with said support member, said second end secured to said slidable member, and said bend engaged with said pouch adjacent said mouth, and said pouch mouth secured to said support member by a tether, said tether having first and second ends secured to said support member and engaging said pouch at a location between said ends of said tether such that sliding said slidable member operates said closure while maintaining the position of said pouch mouth engaged with said interconnecting member adjacent said bend of said interconnecting member.

5. A surgical device for retrieving material from within a patient's body comprising:

an elongated tubular member having a first distal end region insertable into the patient's body and a second proximal end region said distal end region having a diametrical extent that is small compared to the length of the member;

a material retrieval pouch at the distal end region of the tubular member, said pouch having a material receiving mouth leading to a collapsible pouch body; and, a pouch operator for closing and opening said mouth comprising a pouch support reciprocatable within said tubular member in the direction of extent of the tubular member, said pouch support comprising at least a stiffly resilient, flexible pouch support section shiftable between a first, deployed condition wherein said pouch support section projects from the distal end of said tubular member to define an open loop having a diametrical extent substantially greater than the diametrical extent of said tubular member distal end region and a second, retracted condition wherein at least a substantial portion of said pouch support section is disposed within and resiliently confined by said tubular member;

mounting structure connecting said pouch and said pouch support section for relative sliding motion as said flexible pouch support section is operated between said deployed and retracted conditions, said pouch mouth opened for receiving material by said pouch support section as said pouch support section is deployed to form said loop and said pouch mouth substantially closed to secure material within said pouch body when said pouch support section is operated to its retracted condition; and, a tether secured to said pouch at a pouch location adjacent the distal end of said tubular member, said tether comprising a flexible line-like element extending from said pouch location into said tubular member distal end, said tether preventing said pouch location from moving away from said tubular member distal end as said pouch support section is operated to its deployed condition so that said pouch mouth is opened by said pouch support section.

6. The device claimed in claim 5 wherein said tubular member is formed by a generally cylindrical tubular shaft.

7. The device claimed in claim 5 wherein said tubular member is substantially rigid.

8. The device claimed in claim 5 wherein said tether is secured to said tubular member adjacent the proximal end thereof.

9. The device claimed in claim 8 further including a tubular member support body at the proximal end of said tubular member and wherein said tether engages said support body.

10. The device claimed in claim 5 wherein said tether and said pouch support section coextend within said tubular member when said pouch support section is in said retracted condition.

11. The device claimed in claim 5 further including a tubular member support body at the proximal end of said tubular member and a manually operated slidable member associated with the support body for reciprocating sliding movement with respect to said support body, said slidable member connected to said pouch operator for shifting said pouch support section between said conditions.

12. The device claimed in claim 5 wherein said mounting structure for connecting said pouch and said pouch support section comprises a pocket surrounding said mouth, said pouch support section extending through said pocket.

13. A surgical device for retrieving material from within a patient's body comprising:

an elongated tubular member having a first distal end region insertable into the patient's body and a second proximal end region, said distal end region having a diametrical extent which is small compared to the length of said tubular member;

a material retrieval pouch located adjacent the distal end region of the tubular member, said pouch having a material receiving mouth leading to a collapsible pouch body;

a pouch support reciprocatable within said tubular member in the direction of extent of the tubular member, said pouch support comprising at least a stiffly resilient, flexible pouch support section, said pouch support and said tubular member relatively reciprocated to a first position wherein said pouch support section forms an open loop extending from the distal end of said tubular member having a projecting loop portion remote from said distal end, said loop having a diametrical extent greater than the diametrical extent of said tubular member distal end region, said pouch support and said tubular member relatively reciprocated to a second position wherein at least a substantial portion of said pouch support section is disposed within said tubular member;

mounting structure connecting said pouch and said pouch support section, said mounting structure slidably engaging said pouch support section in the vicinity of said pouch mouth so that said pouch mouth is opened and substantially conformed to the shape of said loop when said pouch support section forms said open loop; and, a tether secured to said pouch body at a pouch attachment location adjacent the pouch mouth, the pouch attachment location adjacent the tubular member distal end when the pouch support section is in said first position, said tether comprising a thin flexible element extending within said tubular member and securing said pouch attachment location against moving away from said tubular member distal end toward said projecting loop portion when said pouch support section is in said first position.

14. The device claimed in claim 13 wherein said pouch support and said tubular member are relatively shiftable to a relative position at which said pouch is collapsed and received within said tubular member for insertion in a patient's body.

15. The device claimed in claim 14 wherein said tubular member is an introducer sleeve for introducing said pouch into a patient's body.

16. The device claimed in claim 1 wherein said tubular member is an introducer sleeve for introducing said pouch into a patient's body.

17. A surgical device for retrieving an object from a body, comprising, an operating assembly including a shaft portion having a longitudinal bore extending between first and second ends, a closure portion having a support member engaged with said second end of said shaft portion, a slidable member slidably mounted on said support member for operation of said assembly, and a flexible elongate interconnecting member secured at a first end with said slidable member and engagable with said support member at a second end, a compressible pouch for receiving the object, having a mouth portion secured adjacent said shaft portion first end, and which is movable between an open position and a closed position upon manual operation of said operating assembly, said pouch comprising a pocket surrounding said mouth portion, an introducer sleeve slidably mounted on said shaft portion, and having a longitudinal bore for housing said pouch, said interconnecting member disposed within said shaft portion and said pouch pocket such that manual movement of said slidable member with respect to said support member moves said pouch mouth portion between open and closed positions, said interconnecting member having a bend intermediate its first and second ends to form a first arm between said first end and bend, and a second arm between said bend and second end, said first and second arms engaged within said shaft portion bore and said bend and portions of said first and second arms engaged within said pouch pocket, and, a tether securing said pouch mouth portion adjacent said first end of said shaft portion, said tether having first and second ends secured at the second end of the shaft portion.

18. The surgical device of claim 17, wherein said longitudinal bore of said introducer sleeve has spaced first and second ends and said second end is remote from said slidable member.

19. The surgical device of claim 18, wherein the first end of the shaft portion is configured for engagement with the first end of the introducer sleeve to prevent removal of the sleeve from engagement with the shaft portion.

20. The surgical device of claim 19, wherein the pouch is comprised of a permeable material.

21. The surgical device of claim 19, wherein the pouch is comprised of a nonpermeable material.

* * * * *

(12) EX PARTE REEXAMINATION CERTIFICATE (7163rd)
United States Patent
Younker (10) Number: US 5,643,283 C1
(45) Certificate Issued: Nov. 17, 2009

(54) SURGICAL POUCH

(75) Inventor: Marlin E. Younker, Waite Hill, OH (US)

(73) Assignee: United States Endoscopy Group, Inc., Mentor, OH (US)

Reexamination Request:
No. 90/008,759, Jul. 19, 2007

Reexamination Certificate for:
Patent No.: 5,643,283
Issued: Jul. 1, 1997
Appl. No.: 08/357,368
Filed: Dec. 15, 1994

Related U.S. Application Data

(63) Continuation of application No. 08/215,009, filed on Mar. 21, 1994, now abandoned, which is a continuation of application No. 07/966,902, filed on Oct. 26, 1992, now abandoned, which is a continuation of application No. 07/816,900, filed on Jan. 3, 1992, now abandoned.

(51) Int. Cl.
*A61B 17/00* (2006.01)
*A61B 17/28* (2006.01)
*A61B 17/24* (2006.01)

(52) U.S. Cl. .......................................... 606/17; 606/15

(58) Field of Classification Search ................ None
See application file for complete search history.

(56) References Cited

U.S. PATENT DOCUMENTS

| 460,940 | A | * | 10/1891 | Baught .................... 606/106 |
| 2,197,921 | A | * | 4/1940 | Brown ........................ 43/12 |
| 5,147,371 | A | * | 9/1992 | Washington et al. ...... 606/127 |

* cited by examiner

*Primary Examiner*—David O. Reip (57) ABSTRACT

A surgical device for retrieving an object from inside a body. The device includes a shaft, a compressible pouch for receiving the object positioned adjacent the first end of the shaft. The pouch includes a mouth which may be opened and closed. An introducer sleeve is slidably positioned along the shaft for enclosing the pouch. A slotted support member having a first end affixed to the second end of the shaft, is also provided. Further, a slidable handle member is slidably positioned along the slotted support member, and an interconnecting member extends through the shaft and is interconnected with the handle, pouch and the slotted member for closing and opening the pouch, such that sliding the handle along the slotted member operates to open and close the pouch of the device.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 10, 14 and 15 is confirmed.

Claims 5–7, 11 and 13 are cancelled.

New claims 22 and 23 are added and determined to be patentable.

Claims 1–4, 8, 9, 12 and 16–21 were not reexamined.

22. *A surgical device for retrieving material from within a patient's body comprising:*
   *an elongated tubular member having a first distal end region insertable into the patient's body and a second proximal end region, said distal end region having a diametrical extent that is small compared to the length of the member;*
   *a material retrieval pouch at the distal end region of the tubular member, said pouch having a material receiving mouth leading to a collapsible pouch body;*
   *a pouch operator for closing and opening said pouch mouth comprising a pouch support reciprocatable within said tubular member in a direction of extent of the tubular member, said pouch support comprising at least a stiffly resilient, flexible pouch support section shiftable between a first, deployed condition wherein said pouch support section projects from the distal end of said tubular member to define an open loop having a diametrical extent substantially greater than the diametrical extent of said tubular member distal end region and a second, retracted condition wherein at least a substantial portion of said pouch support section is disposed within and resiliently confined by said tubular member;*
   *mounting structure connecting said pouch and said pouch support section for relative sliding motion as said flexible pouch support section is operated between said deployed and retracted conditions, said pouch mouth opened for receiving material by said pouch support section as said pouch support section is deployed to form said loop and said pouch mouth substantially closed to secure material within said pouch body when said pouch support section is operated to its retracted condition; and*
   *a tether secured to said pouch at a pouch location adjacent the distal end of said tubular member, said tether comprising a flexible line-like element extending from said pouch location into an open mouth aperture of said tubular member distal end and axially along an inner length of said tubular member, said tether preventing said pouch location from moving away from said tubular member distal end as said pouch support section is operated to its deployed condition so that said pouch mouth is opened by said pouch support section.*

23. *A surgical device for retrieving material from within a patient's body comprising:*
   *an elongated tubular member having a first distal end region insertable into the patient's body and a second proximal end region, said distal end region having a diametrical extent that is small compared to the length of the member;*
   *a material retrieval pouch adjacent the distal end region of the tubular member, said pouch having a material receiving mouth leading to a collapsible pouch body;*
   *a pouch support reciprocatable within said tubular member in a direction of extent of the tubular member, said pouch support comprising at least a stiffly resilient, flexible pouch support section, said pouch support and said tubular member relatively reciprocated to a first position wherein said pouch support section forms an open loop extending from the distal end of said tubular member having a projecting loop portion remote from said distal end, said loop having a diametrical extent greater than the diametrical extent of said tubular member distal end region, said pouch support and said tubular member relatively reciprocated to a second position wherein at least a substantial portion of said pouch support section is disposed within said tubular member;*
   *mounting structure connecting said pouch and said pouch support section, said mounting structure slidably engaging said pouch support section in the vicinity of said pouch mouth so that said pouch mouth is opened and substantially conformed to the shape of said loop when said pouch support section forms said open loop; and*
   *a tether secured to said pouch body at a pouch attachment location adjacent the pouch mouth, the pouch attachment location adjacent the tubular member distal end when the pouch support section is in said first position, said tether comprising a thin flexible element entering into an open mouth aperture of said tubular member distal end and axially along an inner length of said tubular member, and securing said pouch attachment location against moving away from said tubular member distal end toward said projecting loop portion when said pouch support section is in said first position.*

\* \* \* \* \*